US005709709A

United States Patent [19]
Kroll

[11] Patent Number: 5,709,709
[45] Date of Patent: Jan. 20, 1998

[54] ICD WITH RATE-RESPONSIVE PACING

[75] Inventor: Mark W. Kroll, Minnetonka, Minn.

[73] Assignee: Angeion Corporation, Plymouth, Minn.

[21] Appl. No.: 600,750

[22] Filed: Feb. 13, 1996

[51] Int. Cl.[6] .................. A61N 1/39; A61N 1/365; A61N 1/362

[52] U.S. Cl. ............. 607/4; 607/122; 607/8; 607/6

[58] Field of Search .............. 607/4–6, 8, 122, 607/126, 127

[56] References Cited

U.S. PATENT DOCUMENTS

| | | | |
|---|---|---|---|
| 4,485,813 | 12/1984 | Anderson et al. | 607/122 |
| 4,702,253 | 10/1987 | Nappholz et al. | 607/20 |
| 4,774,950 | 10/1988 | Cohen | 607/6 |
| 4,901,725 | 2/1990 | Nappholz et al. | 607/20 |
| 5,197,467 | 3/1993 | Steinhaus et al. | 607/20 |
| 5,201,808 | 4/1993 | Steinhaus et al. | 607/20 |
| 5,257,621 | 11/1993 | Bardy et al. | 607/4 |
| 5,336,253 | 8/1994 | Gordon et al. | 607/122 |
| 5,431,681 | 7/1995 | Helland | 607/4 |
| 5,441,524 | 8/1995 | Reuter et al. | 607/18 |
| 5,447,521 | 9/1995 | Anderson et al. | 607/6 |
| 5,531,766 | 7/1996 | Kroll et al. | 607/5 |
| 5,534,022 | 7/1996 | Hoffmann et al. | 607/122 |
| 5,578,064 | 11/1996 | Prutchi | 607/19 |

FOREIGN PATENT DOCUMENTS

560569A2  9/1993  European Pat. Off. ......... 607/5

OTHER PUBLICATIONS

U.S. application No. 08/547275, Kroll, filed Oct. 24, 1994.

*Primary Examiner*—William E. Kamm
*Assistant Examiner*—Carl H. Layno
*Attorney, Agent, or Firm*—Brad Pedersen

[57] ABSTRACT

An implantable cardioverter defibrillator (ICD) system features rate-responsive pacing capabilities. An electrical pulse generating device having a housing containing pulse generating circuitry is provided. A conductive lead connectable to the housing that has a first electrode, a second electrode and a coil electrode is provided. Switching circuitry is provided contained in the housing that switches the coil electrode between the rate-responsive sensing electrode to a defibrillation electrode. Control circuity is provided within the housing for controlling the delivery of modulating signals to the coil electrode and for sensing changes in resistance between the coil electrode and the housing. The control circuitry also causes an alteration of the pacing signal applied to the pacing electrode depending upon the change in the resistance sensed.

6 Claims, 4 Drawing Sheets

ICD WITH RATE-RESPONSIVE PACING

FIELD OF THE INVENTION

The present invention relates to implantable cardioverter defibrillator systems. In particular, the present invention relates to an implantable cardioverter defibrillator system having rate-responsive pacing capabilities.

BACKGROUND OF THE INVENTION

Despite substantial progress over the last several decades, heart disease and its associated dysrhythmia remains one of the most prevalent causes of death in the world. Substantial testing utilizing continuous cardiac monitoring has revealed that prompt detection and diagnosis of cardiac dysrhythmias and rapid treatment allow for reversal of the cardiac dysrhythmias. Diligent physician and nursing intervention can interrupt the natural progression of the patient disease and increase the survival rate. This testing is predicated upon trained personnel being able to recognize and correctly diagnose a patient's cardiac dysrhythmia and then provide the appropriate treatment.

Recent years have shown substantial progress in the development of automatic implantable cardioverter defibrillator systems (ICDs). These electronic standby cardioverter defibrillators will, in response to detection of abnormal cardiac rhythms, countershock the heart muscle via implanted electrodes with sufficient energy to depolarize the heart. This shock technique is directed at abolishing the pathologic dysrhythmia, thereby allowing the natural pacing activity of the heart to reestablish its dominance restoring the normal cardiac rhythm.

Successful ICD systems need electrodes for delivering a shock for defibrillating the heart. Early studies indicated that ventricular fibrillation conversion was achieved when shocks stimulated a critical mass of the heart. Early uses of defibrillators included use of external paddles placed against the chest. As ICDs began to increase in popularity, dual epicardial patches were developed to give a more uniform current density throughout the ventricular mass. With epicardial patches, defibrillation can occur with relatively low energy. The major drawback to the epicardial patches is that they require a thoracotomy or other major surgical procedure. A variety of multipolar transvenous lead systems have been developed in recent years to eliminate the need for thoracotomy or other major surgical procedures for implanting ICDs. Defibrillating electrodes, which are incorporated onto a transvenous lead are usually positioned in the right ventricle and the super vena cava. Due to the relatively small electrode surface area and the position within the heart, highly nonuniform current densities or fields can be produced. Because the blood surrounding the electrodes the veins and heart, has a lower electrical impedance than the myocardial tissue, current may be shunted away from the heart. This current shunting can cause further nonuniformity of the defibrillation electrical fields. The need to provide more uniform current densities and lower energy requirements for defibrillation can be enhanced by transvenous systems that incorporate multiple defibrillating electrodes.

Transvenous lead systems must not only deliver the defibrillation shocks, but provide sensing capabilities. The use of the defibrillating electrodes for monitoring the heart rate is typically not recommended. This is because defibrillation electrodes have a comparatively large surface area which results in an averaging of a great deal of cellular electrical activity thus causing the sensed signal to become non-distinct and difficult to reliably use. Thus, at least one of the electrodes used for monitoring should be of a small surface area to achieve an accurate reading.

Along with the progress in the development of ICD's, there has also been a proliferation of cardiac pacemakers. Pacemakers are generally characterized by which chambers of the heart they are capable of sensing, the chambers to which they deliver pacing stimuli, and the responses, if any, to sense intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence or recognition of the intrinsic electrical events. One type of pacemaker for instance, senses electrical cardiac activity in the ventricle of the patient's heart, and delivers pacing stimuli to the ventricle only in the absence of electrical signals indicative of natural ventricular contractions. Another pacemaker, senses electrical signals in both the atrium and ventricle of the patient's heart and delivers atrial pacing stimuli in the absence of signals indicative of natural atrial contractions, and ventricle pacing stimuli in the absence of signals indicative of natural ventricular contractions.

Pacemakers are also known which respond to other types of physiological based signals, such as signals from sensors for measuring the pressure inside the patient's ventricle or for measuring the level of the patient's physical activity. In recent years, pacemakers which estimate the metabolic demand and vary the pacing rate and response thereto have become widely available. One example of this measures physical activity by means of a piezoelectrical transducer. Such a pacemaker is disclosed in U.S. Pat. No. 4,485,813 to Anderson, et al.

The primary disadvantage of a rate-responsive pacemaker employing a physical activity sensor is the difficulty of obtaining a scaled response through gradations of metabolic demand. Activity sensors generally act in an on/off fashion, in which a sensor is unable to detect changes in patient workload. Therefore, the response of activity based, rate-responsive pacemakers does not normally depend on the amount of exercise the patient is performing, but instead the rate change remains identical so long as the measured activity is above a preprogrammed level.

Furthermore, a physical activity sensor generates an undesirable response to noise disturbances arising external to the body such as car vibrations, etc. Noise disturbances are also realized from within the body for functions such as coughing, sneezing and laughing.

Pacemakers that use metabolic demand sensors for measuring and analyzing impedance signals which relate to a patient's respiratory function to adjust pacing according to the metabolic demands of the patient are also known. The respiratory parameter which correlates most closely to heart rate is minute-volume ventilation which is a highly physiologic variable which reflects closely the metabolic demands of exercise. Minute-volume ventilation is a measure of the amount of air inspired by a person as a function of time. The greater the amount of air inspired, the greater the need for a higher pacing rate.

U.S. Pat. No. 4,702,253 to Nappholz et al. discloses a rate-responsive pacemaker which senses impedance in the pleural cavity of a patient and derives respiratory minute volume from impedance. The minute volume is then used as a rate control parameter. As stated above, the greater the amount of air inspired, the greater the need for a higher pacing rate. The device described in the '253 patent requires a non-standard pacing lead in order to perform the minute-volume measurement.

Other minute-volume rate-responsive pacing systems include U.S. Pat. No. 4,901,725 to Nappholz et al. and U.S. Pat. No. 5,201,808 to Steinhaus et al. The '725 patent discloses a system that derives a minute-volume from a bipolar lead by using an algorithm based on averaged samples and zero crossings to determine the pacing rate. The '808 patent employs a high frequency measuring current which creates a displacement current within the body. The displacement current is then used to detect spacial impedance.

As indicated above, there are numerous known pacing systems. As is well understood by those skilled in the art, pacemaker technology is quite different from ICD technology. For example, a typical defibrillation countershock is on the order of 40 joules while a typical pacing pulse is on the order of 4 microjoules, which is analogous to comparing a go-cart to a MACK™ truck.

With the proliferation of ICD systems being implanted into patients there is now a substantial population who would benefit from both a traditional pacing therapy and the safeguards an ICD system provides. It is desirable to provide an ICD system capable of the traditional ICD functions yet also having rate-responsive pacing capabilities.

SUMMARY OF THE INVENTION

The present provides an implantable cardioverter defibrillator (ICD) system having rate-responsive pacing capabilities. An electrical pulse generating device having a housing containing pulse generating circuitry is provided. A conductive lead connectable to the housing that has a first electrode, a second electrode and a coil electrode is provided. Switching circuitry is provided contained in the housing that switches the coil electrode between a rate-responsive sensing electrode and a defibrillation electrode. Control circuity is provided within the housing for controlling the delivery of modulating signals to the coil electrode and for sensing changes in resistance between the coil electrode and the housing. The control circuitry also causes an alteration of the pacing signal applied to the pacing electrode depending upon the change in the resistance sensed.

Also disclosed in the present invention is a method of using an ICD for rate-responsive pacing. The ICD has a housing with switching circuitry and control circuitry within the housing. A conductive lead connectable to the housing that has a sensing lead, a pacing lead and a coil electrode is provided. The conductive lead is then positioned within the patient's heart. The switching circuitry is then utilized to configure the coil electrode to be a rate-responsive sensing electrode. An electrical signal is then applied to the rate-responsive sensing electrode. The control circuitry then detects the impedance between the rate-responsive sensing electrode and the housing. Finally, the rate of applying pacing pulses is altered in response to the impedance signal detected by the control circuitry which leads to an estimate of minute ventilation.

DETAILED DESCRIPTION OF THE PREFERRED EMBODIMENT

The present invention is an implantable cardiac defibrillator (ICD) system with rate-responsive pacing. The method of rate-responsive pacing described with respect to the preferred embodiment of the present invention will be minute-volume ventilation rate-responsive pacing, however, it should be noted that other methods of rate-responsive pacing are also considered within the spirit and scope of the present invention.

Figure 1:
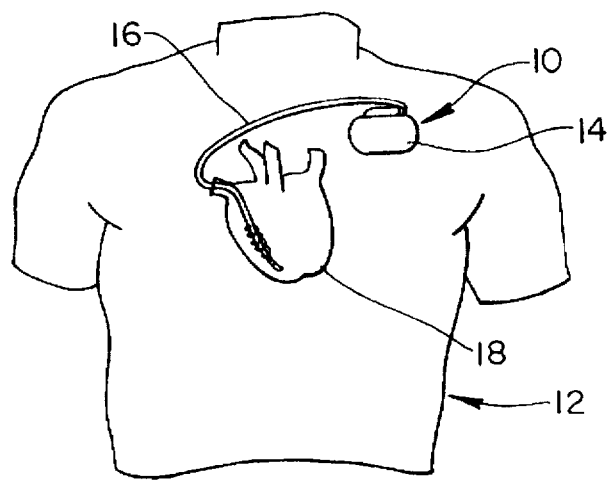
FIG. 1 is a perspective view of a implantable cardioverter defibrillator (ICD) implanted in a human patient.

FIG. 1 is a perspective view of an ICD system 10 implanted in a human patient 12. ICD system 10 includes a housing 14 implanted in a pectoral region of the patient and an electrical lead 16 connected to housing 14 and inserted into heart 18 of the patient. Lead 16 is a bipolar lead as will be described in greater detail in FIG. 2.

Figure 2:
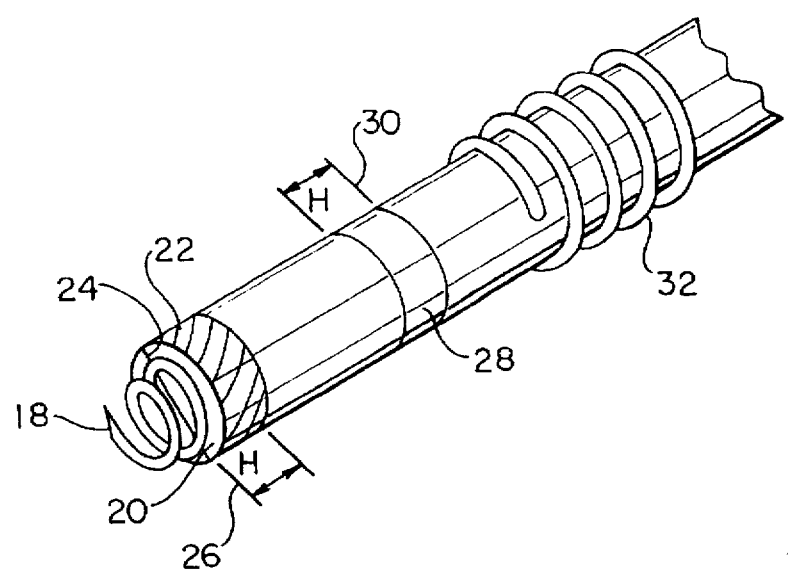
FIG. 2 is a partial perspective view of a bi-polar sensing lead.

FIG. 2 is a partial perspective view of bipolar sensing lead 16. The portion of bipolar lead 16 illustrated is the distal portion of the lead. Bipolar lead 16 includes an anchoring fine 18 connected to a distal end 20 of lead 16. Anchoring tine 18 is depicted as a stiff wire, shaped in the form of a screw that may be actively implanted within the endocardium of a patient's heart with a simple twist applied to the lead by the physician at the time of implantation. Alternatively, anchoring tine 18 may have a plurality of fingers made of silicon or the like for securing bipolar lead 16 to an interior wall of the heart. A first electrode 22 is provided on lead 16 which encompasses distal end 20 of the lead. Electrode 22 is typically called a tip electrode and will be hereinafter referred to as such. Tip electrode 22 is used as a pacing/sensing electrode.

Large surface area electrodes are not particularly well suited for monitoring of the heart rate because they tend to cause an averaging of a great deal of cellular electrical activity causing the signal to be non-distinct and difficult to reliably use for counting, thus, it is important to use at least one small surface area electrode. Tip electrode 22 has a small surface area. Tip electrode 22 has a diameter indicated at line 24 and a height indicated at line 26. In the preferred embodiment, the largest dimension of diameter 24 or height 26 is less than three millimeters which yields a surface area of less than approximately 25 square millimeters. It should be noted that these dimensions are only approximations, and greater or lesser heights and diameters may be used without departing from the spirit or scope of the invention.

The present invention could also use both a large surface area electrode and a small surface area electrode simultaneously to accurately detect R-waves.

Lead 16 also includes a ring electrode 28 spaced approximately 10 millimeters from distal end 20 of the lead. Ring electrode 28 has a height indicated at line 30 substantially similar to the height of tip electrode 22. Together, electrodes 22 and 28 constitute a bipolar pair of electrodes. Also provided on lead 16 is a right ventricular (RV) defibrillation coil electrode 32. RV coil 32 is spaced approximately six millimeters from ring electrode 28. Greater or lesser spacing between ring electrode 28 and RV coil 32 may be used without departing from the spirit or scope of the present invention.

In the preferred embodiment of the present invention, coil electrode 32 is used both as a defibrillation coil and as a rate-responsive sensing coil. In known pacemaker systems that utilize rate-responsive pacing, small surface area pacing electrodes are used for both the sensing and the pacing functions. Because the pacing electrodes are typically small, they sense only local activity. Additionally, there is a problem is separating the cardiac signal and the rate-responsive signal due to spectral overlap. One approach to solving the problem of spectral overlap is extreme filtering, but this has the drawback of adding components which increases both the size and power consumption. The present invention overcomes the drawbacks of the known pacing systems by utilizing a large surface area coil such as defibrillation coil 32 as the rate-responsive sensing coil. This allows the sensing coil to sense a larger area because of its size and also avoids the problem of spectral overlap since the rate-responsive sensing is done through different electrodes than electrogram sensing is done through. Additionally, pacing can be performed continuously without the need of any special correction for the influence of the pacing signal on the pacing/sensing line as is necessary with the known rate-responsive pacing systems because the present invention has a separate sensing electrode from the pacing electrode.

Figure 3:
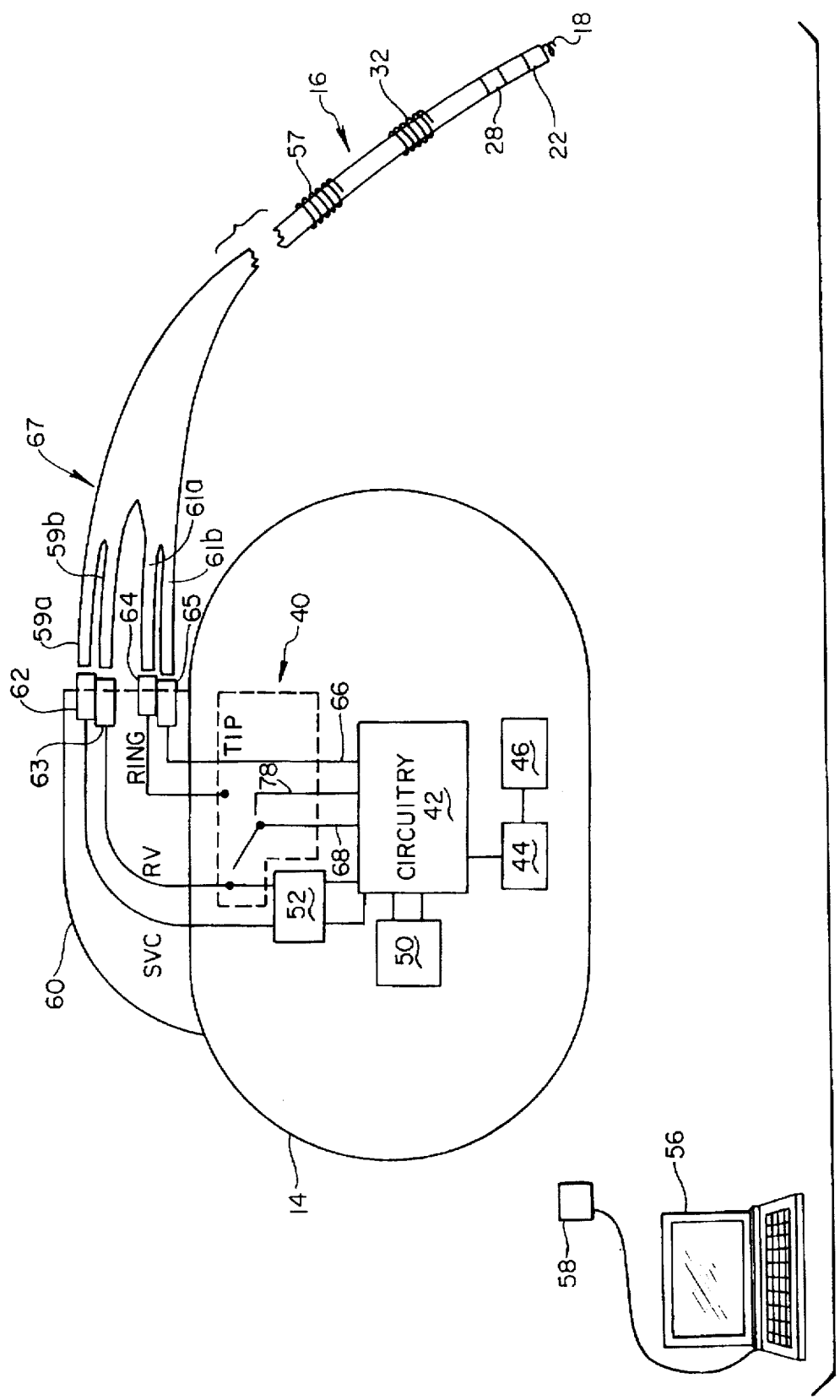
FIG. 3 is a schematic diagram of an ICD system in accordance with the present invention.

In order to utilize coil 32 as both a rate-responsive sensing coil and a defibrillation coil, ICD system 10 of the present invention contains switching circuitry 40 inside housing 14 as illustrated in FIG. 3. Housing 14 also includes digital and analog control circuitry 42, a microcomputer 44 and memory 46, a telemetry receiver antenna 50 and a high voltage output system 52 all connected to circuitry 42. Also illustrated in FIG. 3 is an operator interface console 56 and an ICD interface 58 for allowing remote communication with the ICD. Housing 14 also includes a header 60 that has connecting ports 62, 63, 64 and 65. Header 60 is mounted onto the housing, but could also be integrally formed as part of the housing. Additionally, connecting ports 62, 63, 64 and 65 could be formed directly in housing 14.

Lead 16 is illustrated in FIG. 3 with anchoring tine 18, tip electrode 22, ring electrode 28 and RV coil electrode 32 as in FIG. 2. FIG. 3 also illustrates lead 16 having a super vena cava defibrillating electrode 57 and connection ends 59a, 59b and 61a, 61b at a proximal end 67 of the lead. Connection ends 59a, 59b are connectable to connection ports 62, 63, respectively and connection ends 61a, 61b are connectable to connection ports 64, 65, respectively. Connection ends 59a, 59b contain high voltage conductors (not shown) which connect to electrodes 57 and 32, and connection ends 61a, 61b contain conductors (not shown) which connect to tip electrode 22, and ring electrode 28.

Switching circuitry 40 is illustrated in FIG. 3 as a mechanical switch for ease of understanding, but it should be realized that mechanical switches are not the preferred embodiment. The switches used are actually electronic switches in the form of components such as bipolar transistors (BJTs), metal oxide semiconductor field effect transistors (MOSFETs), and silicon controlled rectifiers (SCRs). It should be noted that these are only a few examples and they are not meant to be an exclusive list of components which could be used. An electrode receiving line 66 is provided between connection port 65 and circuitry 42, and another electrode receiving line 68 is connected to circuitry 42 and switching circuitry 40. A select line 78 which comes from circuitry 42 is provided for controlling the operation of switching circuitry 40.

In order to protect the circuitry and the sensing electrodes, a protection routine is provided. The protection routine of this embodiment is preferably a software based system that resides in microcomputer 44, although a hardware implementation of the protection routine could also be utilized. In essence, the protection routine causes all non-essential components for the high voltage output to effectively act as open circuits for a period of time. This is called a blanking routine. In particular, microcomputer 44 detects that a high voltage pulse is needed. It then alerts circuitry 42 that a pulse is coming and instructs circuitry 42 to execute the blanking routine. The period chosen in this embodiment is approximately 15–20 ms, but greater or lesser periods of time may be chosen. By waiting a time period such as this, residual charges left on any lines are given time to dissipate, thus avoiding damage to circuitry 42 from a defibrillation shock.

Operator interface console 56 is provided to allow a physician to monitor both past and real time performance of ICD system 10, and to allow the physician to program commands into the ICD. Communication to the ICD is achieved via ICD interface 58. ICD interface 58 is a telemetry transmitter and receiver that allows an operator to communicate to receiver and antenna 50 of the ICD remotely. In the embodiment illustrated, ICD system 10 is a low power system, therefore, ICD interface 58 must be held fairly close to where the ICD is implanted in a patient in order to ensure proper signal transmission. It should be understood that greater distances may be achieved in an increased power system.

Figure 4:
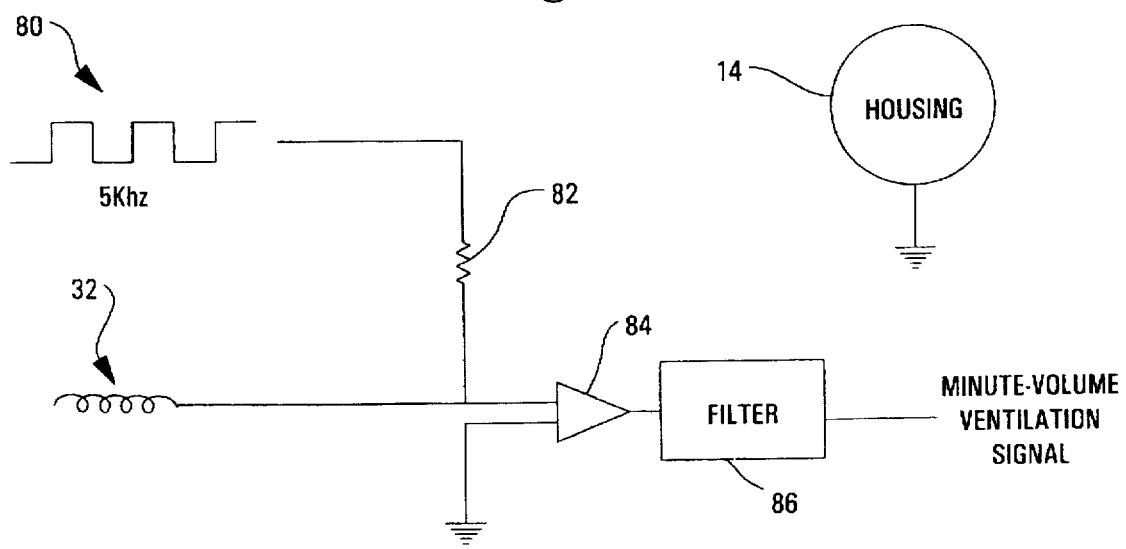
FIG. 4 is a schematic diagram of a minute-volume ventilation signal sensing circuit in accordance with the present invention.

A simple schematic of the minute-volume ventilation signal sensing circuit 79 is illustrated in FIG. 4. This circuit is located within circuitry 42 inside housing 14. A modulating frequency signal 80 is provided to the circuit. In the preferred embodiment of the present invention, modulating signal 80 has a frequency of approximately 5 kilohertz. It should be noted that greater or lesser frequencies may be used without departing from the spirit or scope of the invention. Ventilation signal sensing circuit 79 also includes a resistor 82, an amplifier 84 and a low pass filter 86.

In operation, with coil electrode 32 configured as a rate-responsive sensing coil, a modulating signal 80 is applied to coil 32 through resistor 82. Changes in respiration will cause changes in the resistance between coil 32 and housing 14. This difference will result in a change in the voltage division of the modulated signal 80 which is in turn amplified by amplifier 84. The output of amplifier 84 is then filtered in low pass filter 86 to remove the 5 Khz modulating signal. In the preferred embodiment of the present invention, low pass filter 86 is a 1 Khz low pass filter, but larger or smaller filters may be used without departing from the spirit or scope of the invention. The output of filter 86 is the minute-volume ventilation signal. This signal is then passed along to the control circuitry inside housing 14. The control circuitry reads the minute-volume ventilation signal, and if the signal has increased from the previous sensing cycle, the rate of pacing pulses will be increased appropriately. If the minute-volume signal has decreased, the rate of pacing pulses will be decreased accordingly.

Figure 5:
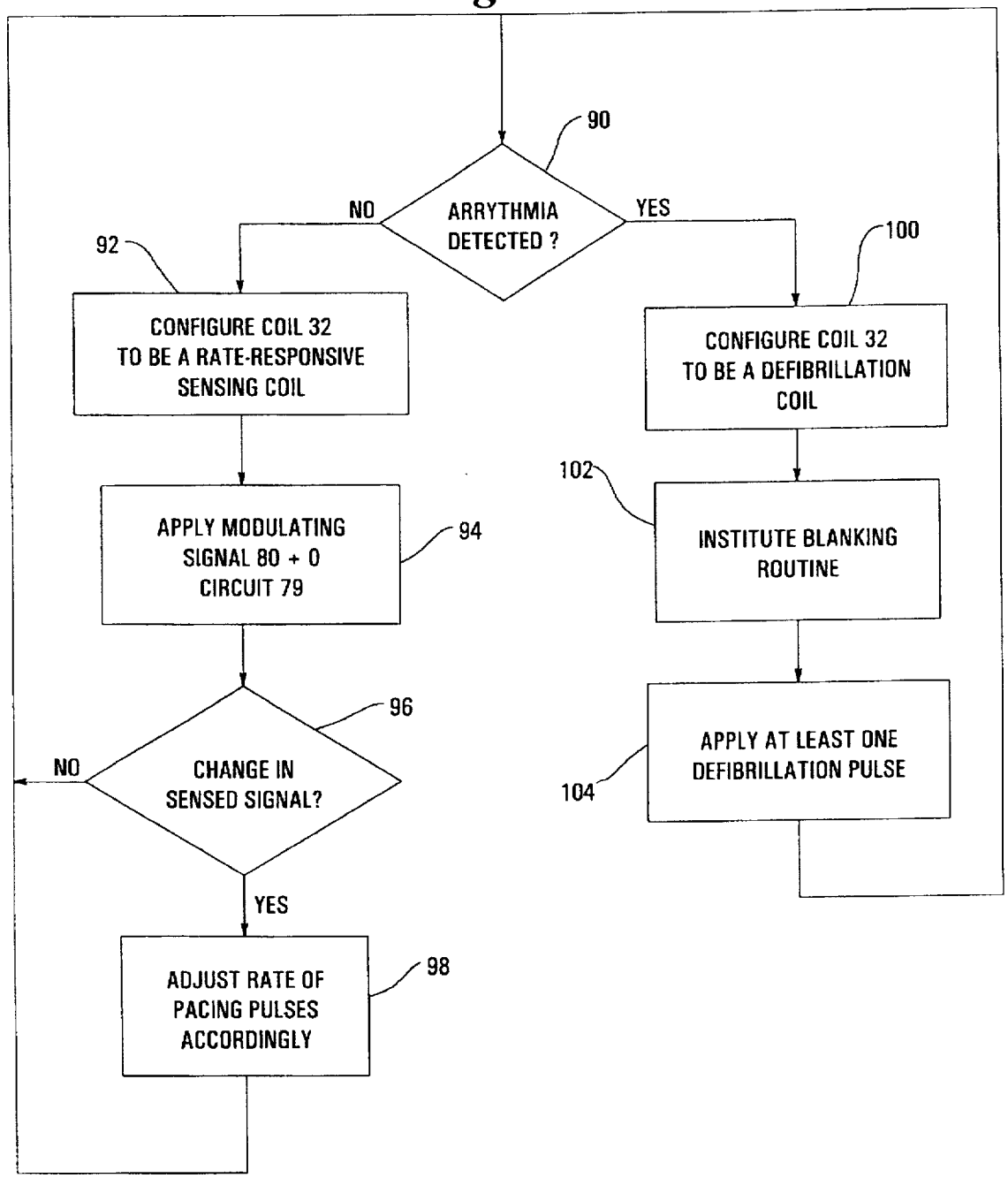
FIG. 5 is a flow chart of a switching routine for the present invention.

FIG. 5 is a flow chart that illustrates the general operation of the ICD system of the present invention. The first block in the flow chart is decision block 90, in which an arrythmia is or is not detected. If an arrythmia is not detected the flow chart follows the left hand path and if an arrythmia is detected the right hand path is followed. Assuming there is no arrythmia detected, coil electrode 32 is then configured to be a rate-responsive sensing coil, as indicated in block 92. Modulation signal 80 is then applied to circuit 79, as indicated in block 94. Decision block 96 then asks if there has been a change in the minute-volume ventilation signal. If yes, then the rate of applying pacing pulses is adjusted accordingly, as illustrated in block 98. After adjusting the pacing pulses, or if there is no change in the minute-volume ventilation signal, the flow chart branches back to decision block 90.

Now assuming an arrythmia was detected in block 90, coil electrode is then configured to be a defibrillation coil, as indicated in block 100. The blanking routine discussed above is then instituted, as illustrated in block 102. At least one defibrillation pulse is then applied to coil 32, as indicated in block 104. At this point, the flow chart branches back to decision block 90.

The pacing pulses applied to tip electrode 22 are on the order of 4 microjoules, and may be in the range of 0.1 to 400 microjoules. The defibrillation pulses applied to coil 32 are on the order of 40 joules, but may be as low as 1 joule and as high as 45 joules.

The above description is just one operation scheme that may be implemented with the present invention. Many other operating formats may be implemented without departing from the spirit or scope of the invention. For instance, it would be possible to program how often the minute-volume ventilation signal should be sensed. In the above operation, the signal is continuously sensed.

I claim:

1. An implantable cardioverter defibrillator system with rate responsive pacing which sense a minute-volume ventilation rate of a patient by the passage of a current between a coil electrode and a housing of the ICD system, the ICD system comprising:

an electrical pulse generating device having a housing containing pulse-generating circuitry therein;

a conductive lead connectable to the housing wherein the lead has a first electrode, a second electrode and a coil electrode;

switching circuitry contained in the housing and operatively connected to the coil electrode, the pulse-generating circuitry and the housing that selectively switches the coil electrode between a rate-responsive sensing mode in which the coil electrode is connected to the housing as part of a circuit for sensing the minute-volume ventilation rate of the patient and a defibrillation mode in which the coil electrode is connected to the pulse-generating circuitry to selectively deliver electrical therapy to the patient; and control circuitry contained within the housing wherein the control circuitry controls the generation and delivery of both pacing signals and defibrillation countershocks by the pulse-generating circuitry, controls the delivery of a modulating signal to the coil electrode when the coil electrode is in the rate-responsive sensing mode, and senses changes in impedance between the coil electrode and the housing causing an alteration of a rate at which the pacing signals are delivered.

2. The system as in claim 1 wherein the coil electrode has an effective length of at least 10 mm.

3. The system as in claim 1 wherein the housing forms an electrode.

4. The system as in claim 1 wherein the impedance changes are measured as a function of the modulating signal.

5. The system as in claim 1 wherein the first electrode comprises a tip electrode.

6. The system as in claim 1 wherein the second electrode comprises a ring electrode.

* * * * *